US00PP25681P3

(12) United States Plant Patent
Schoone

(10) Patent No.: US PP25,681 P3
(45) Date of Patent: Jul. 7, 2015

(54) ***PHALAENOPSIS* ORCHID PLANT NAMED 'NEW DAY'**

(50) Latin Name: ***Phalaenopsis* hybrid**
Varietal Denomination: New Day

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 218 days.

(21) Appl. No.: 13/573,580

(22) Filed: Sep. 26, 2012

(65) Prior Publication Data

US 2013/0081176 P1 Mar. 28, 2013

Related U.S. Application Data

(60) Provisional application No. 61/540,343, filed on Sep. 28, 2011.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
*Assistant Examiner* — Keith Robinson
(74) *Attorney, Agent, or Firm* — Foley & Lardner LLP; Sunit Talapatra

(57) ABSTRACT

A new and distinct *Phalaenopsis* plant named 'New Day' particularly characterized by flowers which are white with a light purple haze and flared purple marks on the edges; the labellum is white with some yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'New Day'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'New Day'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'New Day' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'New Day' originated from a cross made by the inventor in 1999 in Strengweg, Heemskerk, The Netherlands. The female or seed parent is the *Phalaenopsis* cultivar designated 'Happy Valentine', unpatented. The male or pollen parent is the *Phalaenopsis* cultivar designated 'Chain Xen Diamond', unpatented. The new *Phalaenopsis* 'New Day' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture (mericloning) was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'New Day', which in combination distinguish this *Phalaenopsis* as a new and distinct cultivar:

1. flowers which are white with a light purple haze and flared purple marks on the edges; the labellum is white with some yellow and purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'New Day', the female parent 'Happy Valentine' has dark pink flowers, the male parent 'Chain Xen Diamond' has white/violet colored flowers with purple marks, whereas the flowers of 'New Day' are white with a light purple haze and flared purple marks on the edges.

Presently, the commercial cultivar to which 'New Day' can be meaningfully compared is 'Magic Art' (unpatented). They both are white and have flared purple marks on the edges, but the purple haze of 'Magic Art' is darker and 'Magic Art' also has more purple spots. The labellum of 'New Day' has more white and is a lighter color purple.

BRIEF DESCRIPTION OF THE PHOTOGRAPHS

The accompanying photographs illustrate the overall appearance of the new *Phalaenopsis* 'New Day' showing the colors as true as is reasonably possible with colored reproductions of this type. Colors in the photographs may differ slightly from the color values cited in the detailed botanical description, which accurately describe the color of 'New Day'.

DETAILED BOTANICAL DESCRIPTION

Figure 1:
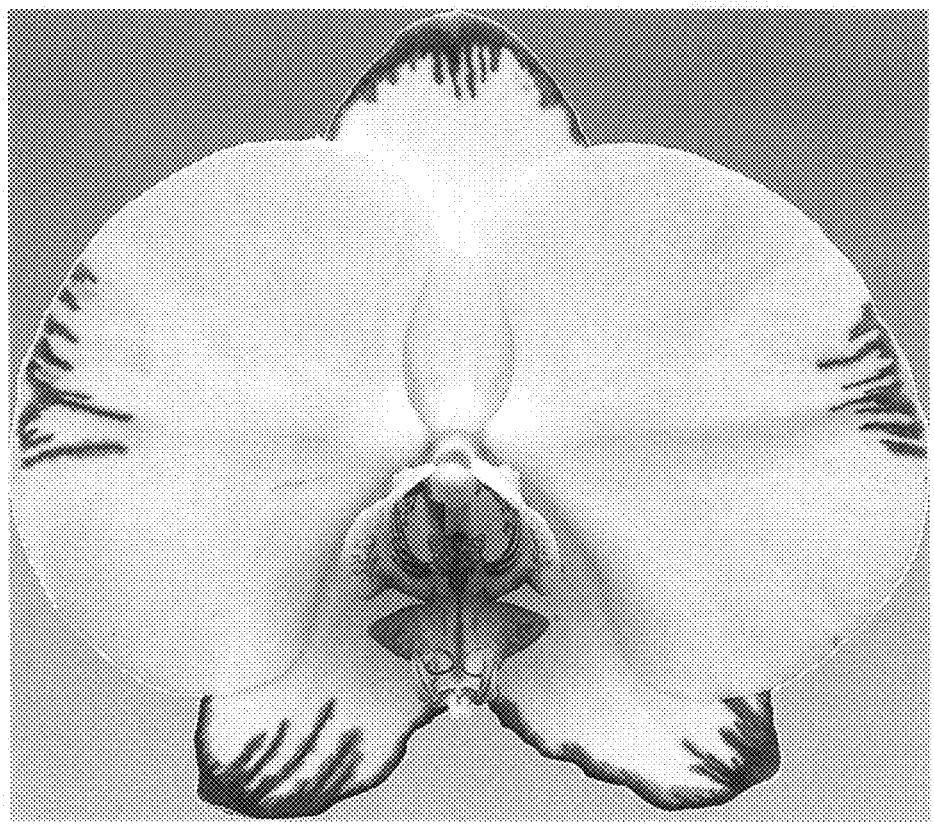
FIG. 1 shows a close-up view of the typical flower of 'New Day'.

The new *Phalaenopsis* cultivar 'New Day' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'New Day' as grown in a greenhouse in Strengweg, Heemskerk, The Netherlands, under conditions which closely approximate those generally used in commercial practice. Initially, the ideal temperature to grow plants of 'New Day' is 27° C. during the day and at night. Then, during the flowering phase of 'New Day', the ideal growing temperature is 20-22° C. during the day and 18° C. at night. Light levels for growing 'New Day' are a minimum of 5,000 lux and a maximum of 10,000 lux. A balanced fertilizer with level of 200 ppm N, 87 ppm P, 168 ppm K is applied. Duration of growth of 'New Day' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'New Day' plants described is 12 months after potting.

Classification:

*Botanical.*—*Phalaenopsis* hybrid.

Parentage:

*Female or seed parent.*—*Phalaenopsis* cultivar designated 'Happy Valentine', unpatented.

*Male or pollen parent.*—*Phalaenopsis* cultivar designated 'Chain Xen Diamond', unpatented.

Propagation:

*Type.*—Tissue culture (mericloning).

*Rooting habit and description.*—Approximately 4 mm-8 mm wide and green/yellow in color (RHS 146C); freely branching. It takes 12 weeks for plants growing in tissue culture to initiate roots.

Plant:

*Size at maturity.*—Height (from bottom of pot to highest flower): about 63 to 70 cm. Spread: about 45 to 58 cm.

*Growth habit.*—Standard; green leaves (RHS 139A) and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, long, tip is blunt and asymmetric.

*Texture (both surfaces).*—Smooth and leathery.

*Pubescence.*—None.

*Base.*—Acute.

*Margin.*—Entire.

*Mature leaf length.*—About 16 to 23 cm.

*Mature leaf width.*—About 8 to 10 cm.

*Mature leaf thickness.*—About 2 mm.

*Mature leaf color.*—Upper surface: green (RHS 139A). Under surface: green (RHS 137B).

*Venation.*—Pattern: parallel. Color of midvein: Upper surface: green (RHS 139A). Under surface: green (RHS 137D).

Raceme:

*Quantity per plant.*—About 1 to 2.

*Number of flowers per raceme.*—About 6.

*Length.*—About 56 cm to 68 cm.

*Diameter.*—About 5 mm to 7 mm.

*Strength.*—Strong.

*Aspect.*—Upright.

*Texture.*—Glabrous and smooth.

*Color.*—Green (RHS 137B).

*Internode.*—Length: about 40 to 50 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 22 to 31 mm. Diameter (at midpoint): about 20 to 33 mm. Shape: egg-shaped. Color: yellow/green (RHS 144B), ends are purple (RHS N79A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1 to 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
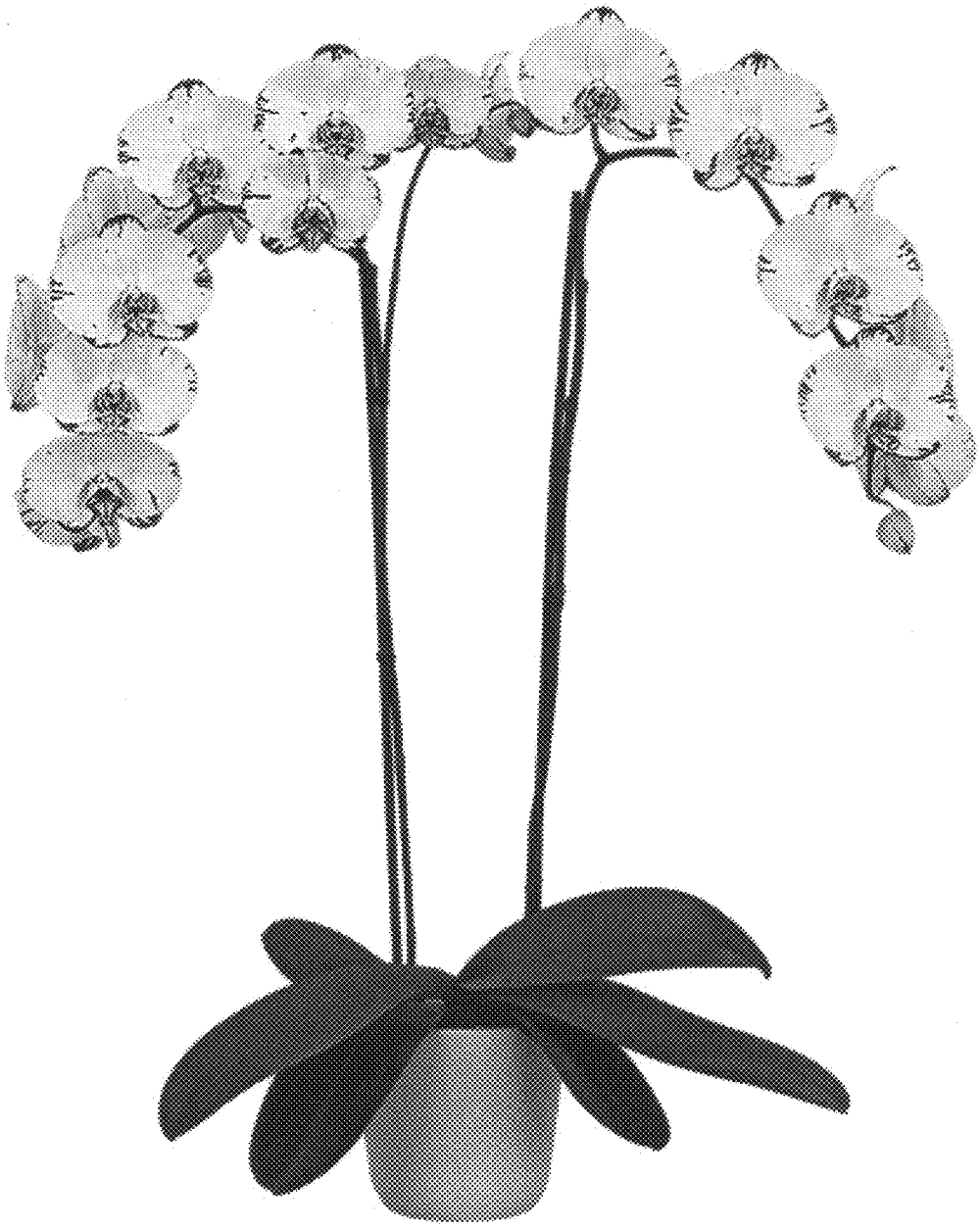
FIG. 2 shows a side view of a typical flowering plant of 'New Day'.
Figure 3:
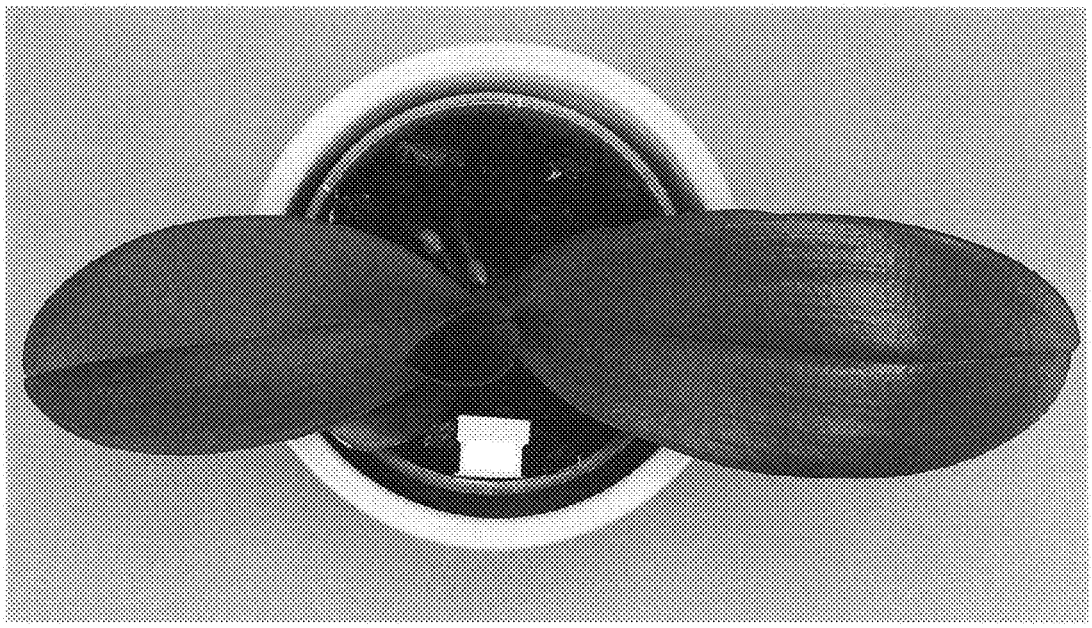
FIG. 3 shows a close-up view of the typical leaves of 'New Day'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 100 mm. Diameter: about 110 mm. Quantity and arrangement: six petals and sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 65 mm. Width: about 55 mm. Texture: Upper surface: smooth and satiny. Under surface: smooth and satiny. Color (when fully opened): Upper surface: main color is white (RHS NN155C) with a violet haze (RHS 84C) and some petals have purple spots (RHS N80B). At the edges flared purple marks (RHS N79C). Under surface: main color is white (RHS NN155C) with a violet haze (RHS 84C and 84D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Length: about 24 mm. Width (not flattened): about 23 mm. Depth of tube (made from lateral lobes of labellum): about 20 mm. Texture: Upper & under surface: smooth and satiny. Color (when fully opened): Upper surface, mid lobe: main color is white (RHS NN155C) with a yellow line in the center (RHS 5C). The upper sides are orange/yellow (RHS 17A) with purple/red spots (RHS 71A) which grow to the cirrhi. The mid vein is red/purple (RHS 71A). Lateral lobes: white (RHS NN155C) with yellow/orange lower edges (RHS 17B). At the base orange/red stripes. On the rest purple stripes (RHS 77B). Under surface: mid lobe: white (RHS NN155C) with some yellow in the center (RHS 13C), some orange/yellow at the sides (RHS 17C) and some red/purple spots (RHS 71A). Lateral lobes: white (RHS NN155C) with yellow/orange edges (RHS 16A) and some purple marks/stripes (RHS 77B). Cirrhi: long and curly. Color: purple (RHS N77B) and white (RHS NN155C). Pestle (Callosities): Length: about 6 mm. Width (not flattened): about 7 mm. Height: about 9 mm. Color: Base is white (RHS NN155C) with on top yellow (RHS 7B) with orange/red strips and spots (RHS N34A).

*Sepals*.—Arrangement: Outer whorl comprises 3 sepals. Overall shape: elliptical and weakly cupped. Dorsal lobe is larger than lateral lobes. Length: about 50 to 58 mm. Width: about 30 to 40 mm. Texture: Upper & under surface: smooth and satiny. Color (when fully opened): Dorsal sepal, upper surface & under surface: main color is white (RHS NN155C), at the base a violet haze (RHS 84C). On the edges flared purple marks (RHS N79C) on the rest some small purple spots (RHS N80B). Lateral sepals, upper surface: same as dorsal sepal only at the base a yellow/green haze (RHS 145D) and flared red/purple marks (RHS 70B). Under surface: same as upper surface only without the red/purple marks.

*Pedicel*.—Length: about 40 to 50 mm. Diameter: about 4 mm. Texture: glabrous and smooth. Color: at the base purple (RHS N79B), in the center green (RHS 138C) and close to the flower red/purple (RHS 74D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 12 mm. Diameter: about 8 mm. Color: white (RHS NN155C) with a purple mark (RHS 77B).

*Pollinia*.—Quantity: Two. Size: about 1 mm. Color: orange (RHS 26).

*Ovary*.—Length: about 4 mm. Diameter: about 7 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'New Day', as illustrated and described herein.

* * * * *